(12) United States Patent
Van Beek et al.

(10) Patent No.: US 7,583,380 B2
(45) Date of Patent: Sep. 1, 2009

(54) SPECTROSCOPIC ANALYSIS APPARATUS AND METHOD WITH EXCITATION SYSTEM AND FOCUS MONITORING SYSTEM

(75) Inventors: Michael Cornelis Van Beek, Eindhoven (NL); Peter Ferdinand Greve, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 319 days.

(21) Appl. No.: 10/547,971

(22) PCT Filed: Mar. 1, 2004

(86) PCT No.: PCT/IB2004/050167

§ 371 (c)(1),
(2), (4) Date: Jun. 30, 2006

(87) PCT Pub. No.: WO2004/081549

PCT Pub. Date: Sep. 23, 2004

(65) Prior Publication Data

US 2006/0258942 A1 Nov. 16, 2006

(30) Foreign Application Priority Data

Mar. 11, 2003 (EP) .................................. 03100610

(51) Int. Cl.
*G01J 3/30* (2006.01)
(52) U.S. Cl. ................. 356/317; 250/201.2; 250/201.3; 250/201.4
(58) Field of Classification Search ................. 359/383; 356/445, 301, 317–318, 417–418, 624, 364; 250/201.2, 201.3, 201.4, 458.1–461.2; 600/317, 600/371; 422/82.07–82.08; 436/172
See application file for complete search history.

(56) References Cited

U.S. PATENT DOCUMENTS 3,847,485 A * 11/1974 Zanoni ........................ 356/624

(Continued)

FOREIGN PATENT DOCUMENTS

EP 1 091 229 A2 4/2001

(Continued)

OTHER PUBLICATIONS

Garcia, J., et al.; Chromatic Aberration and Depth Extraction; 2000; Proc. Pattern Recognition-IEEE Comput. Soc.; pp. 762-765.

*Primary Examiner*—Tarifur Chowdhury
*Assistant Examiner*—Michael Lapage

(57) ABSTRACT

The present invention relates to an analysis apparatus, in particular a spectroscopic analysis apparatus, for analyzing an object, such as blood of a patient, and a corresponding analysis method. To aim the confocal detection volume inside a blood vessel orthogonal polarized spectral imaging (OPSI) is used to locate blood capillaries in the skin. An imaging system (img) with slightly shifted imaging planes (i1, i2) for OPS imaging of blood vessels is proposed to provide auto-focusing. The confocal Raman detection plane (dp) is located in between these two imaging planes (i1, i2). Based on measured amount of defocus for the imaging planes (i1, i2), the focusing of the imaging system (img), the excitation system (exs) for exciting the target region and the detection plane (dp) is located inside the blood vessel (V). Thus, continuous auto-focusing with high accuracy can be achieved. The invention relates also to an optical tracking system for continuously tracking a point of a moving object (obj).

20 Claims, 4 Drawing Sheets

U.S. PATENT DOCUMENTS

Figure 1:
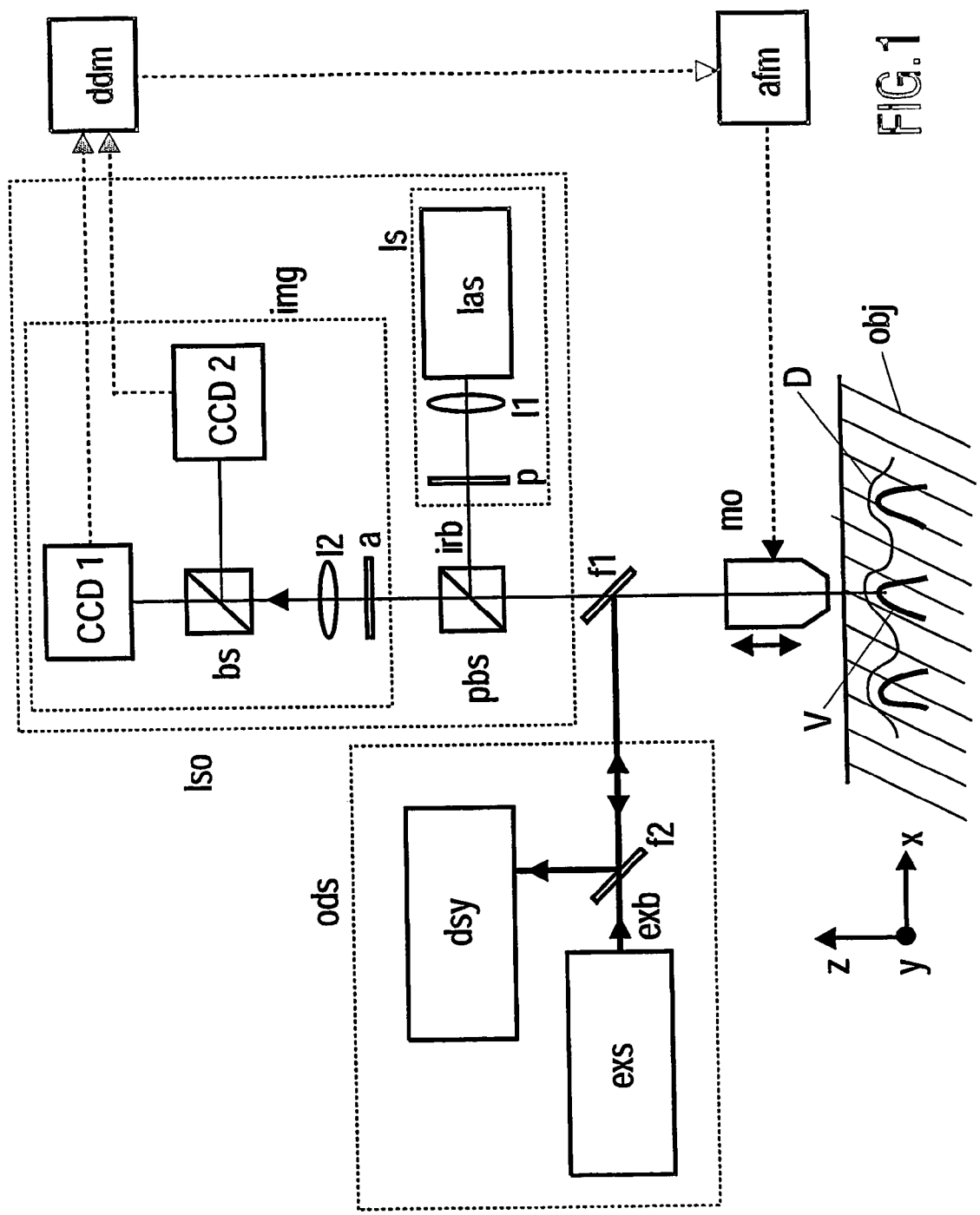

| | | | |
|---|---|---|---|
| 4,844,617 A * | 7/1989 | Kelderman et al. | 356/624 |
| 5,033,856 A * | 7/1991 | Nose et al. | 356/609 |
| 5,294,804 A * | 3/1994 | Kajimura | 250/559.31 |
| 6,008,894 A | 12/1999 | Schmucker et al. | |
| 2002/0133065 A1 | 9/2002 | Lucassen et al. | |
| 2003/0112504 A1* | 6/2003 | Czarnetzki et al. | 359/383 |
| 2003/0142398 A1* | 7/2003 | Leblans | 359/383 |

FOREIGN PATENT DOCUMENTS

| | | |
|---|---|---|
| JP | 7306135 | 11/1995 |
| WO | WO 97/04348 A1 | 2/1997 |
| WO | WO 01/39665 A2 | 6/2001 |
| WO | WO 01/88590 A1 | 11/2001 |
| WO | WO 02/057759 A1 | 7/2002 |

* cited by examiner

SPECTROSCOPIC ANALYSIS APPARATUS AND METHOD WITH EXCITATION SYSTEM AND FOCUS MONITORING SYSTEM

The present invention relates to an analysis apparatus, in particular a spectroscopic analysis apparatus, for analyzing an object, such as the blood of a patient, and a corresponding analysis method. Further, the invention relates to an optical tracking system for continuously tracking a point of a moving object.

In general, analysis apparatuses, such as spectroscopic analysis apparatuses, are used to investigate the composition of an object to be examined, e.g. to measure the concentration of various analytes in blood in vivo. In particular, analysis apparatuses employ an analysis, such as a spectroscopic decomposition, based on interaction of the matter of the object with incident electromagnetic radiation, such as visible light, infrared or ultraviolet radiation.

A spectroscopic analysis apparatus comprising an excitation system and a monitoring system is known from WO 02/057759 A2 which is incorporated herein by reference. The excitation system emits an excitation beam to excite a target region during an excitation period. The monitoring system emits a monitoring beam to image the target region during a monitoring period. The excitation period and the monitoring period substantially overlap. Hence the target region is imaged together with the excitation, and an image is formed displaying both the target region and the excitation area. On the basis of this image, the excitation beam can be very accurately aimed at the target region.

The analysis method known from WO 02/057759 A2 for simultaneous imaging and spectral analysis of a local composition is done by separate lasers for confocal video imaging and Raman excitation or by use of a single laser for combined imaging and Raman analysis. Orthogonal polarized spectral imaging (OPSI), which is also described in WO 02/057759 A2, is a simple, inexpensive and robust method to visualize blood vessels close to the surface of organs which can also be used to visualize blood capillaries in the human skin. Blood capillaries close to the skin surface have a diameter of about 10 µm. Due to confocal detection the source of collected Raman signals is well confined in all three dimensions inside a spot of a size smaller than $5 \times 5 \times 5$ µm$^3$. This allows collecting Raman signals from blood without background signal from skin tissue if the focus is located in a blood capillary. This spot location is possible if the lateral position of the blood vessel as well as the depth of the vessels below the skin surface are known with a resolution of 1 µm or better.

Because of an effective back-illumination of blood vessels, OPSI is essentially a 2-dimensional technique. The only depth information is obtained by the influence of the amount of (de)focus on the images. If an objective with a numerical aperture (NA) higher than 0.8 is used, the depth of field in skin is below 0.5 µm. Therefore, with accurate focusing algorithms based on image analysis it is possible to find the depth of the blood vessel.

Known auto-focusing methods are based on scanning the axial position of the objective focusing the imaging beam and the confocal excitation beam onto the object of interest, while measuring the value of a merit function to quantify the amount of (de)focus. The best focus is found by optimizing the value of the merit function. In general there are many possibilities to change the focus position. For instance, one or two lenses in the objective can be moved (as in a photo camera) or another lens in the system can be moved. Also the shape of an optical element in the system can be changed, for example an electro wetting optical element. However, if the object is not known, the maximum of the merit function is also unknown. Therefore, the merit function provides only information about the amount of focus in relation to other focus positions.

Patients, however, will move in lateral as well as in transversal directions. Therefore, continuous measurement and adjustment of the optimal location of the confocal detection center is required. Transversal movements in the image plane can easily be detected, whereas axial movements (perpendicular to the detection plane) are much more difficult to detect. A common method of detecting axial movement or defocus is by continuously moving the detection plane around the central best focus position (so called wobbling). This can be done by moving the imaging objective or another optical element in the imaging system. If the focus becomes better in front or behind the central position, the central position of the objective is changed. In known systems the detection volume is located in the image plane. Therefore this detection volume is also continuously moved around the best measurement position. This has the disadvantage that the confocal detection volume is located inside a blood vessel for only a fraction of time, and to avoid mixing of skin spectra with blood spectra, the intake of Raman signal has to be gated. This increases the time needed to collect sufficient Raman signal, which is in case of continuous recording already at least 30 sec.

Further disadvantages are, that due to changes in the blood flow the shape and size of a capillary change continuously; so that comparing images acquired at different times add uncertainty to the position of best focus. Additionally, the fact that more time is needed to collect sufficient Raman signal adds to the noise in the Raman spectrum because more dark current is acquired or because more readout noise is added.

It is therefore an object of the present invention to provide an optimized analysis apparatus and a corresponding analysis method for imaging and spectroscopic analysis of an object which allow continuous accurate auto-focusing of the excitation beam onto the object, in particular a blood vessel, even during movements of the object without changing the position of the detection volume continuously.

This object is achieved according to the present invention by an analysis apparatus as claimed in claim 1 comprising:

an excitation system for emitting an excitation beam to excite a target region, a monitoring system comprising a monitoring beam source for emitting a monitoring beam and an imaging system to image the target region, a detection system for detecting scattered radiation from the target region generated by the excitation beam, focusing means for focusing the imaging system on at least two substantially parallel imaging planes at a predetermined distance and for focusing the detection system and the excitation system on a detection plane substantially parallel and in-between the imaging planes at predetermined distances, defocus detection means for determining the amount of defocus of the imaging system from the detection plane for the at least two imaging planes, and auto-focusing means for controlling the focusing means to commonly change the focusing of the imaging system, the excitation system and the detection system based on the determined amount of defocus and the predetermined distances between the imaging planes and the detection plane such that the difference between the determined amount of defocus for the at least two imaging planes equals a predetermined amount.

The object is further solved by a corresponding analysis method described herein. Preferred embodiments of the invention are defined in the dependent claims.

The invention is based on the idea to take at least two images of the object of interest (e.g. a blood vessel) at different imaging planes (focusing planes), i.e. the imaging planes of the imaging system are slightly separated in axial direction (direction of the monitoring beam). The confocal Raman detection center, i.e. the detection plane onto which the excitation beam emitted by the excitation system for exciting the target region (the blood vessel) and the detection system are focused, is located in between these two imaging planes whereby the distances between the imaging planes and the detection plane are predetermined and known. The amount of defocus of the imaging system, i.e. of the at least two images acquired at the imaging planes, is determined with a merit function by the defocus detection means. Since the size and shape of the object of interest (e.g. blood vessels) are not known the merit function provides only a relative amount of defocus. This (relative) amount is then used for control of the focusing means to adjust the position of the detection plane and the imaging planes in common such that the difference between the determined amount of defocus for the at least two imaging planes equals a predetermined amount for the at least two imaging planes. With this information the Raman confocal detection volume can be continuously located exactly inside the object of interest (such as a blood vessel).

Compared to other known auto-focusing techniques the present invention provides the advantage that the confocal detection volume is continuously located in the center of the object of interest, even if the object moves during the measurement. According to preferred embodiments no moving elements are required and a single microscope objective, having a high numerical aperture can be used as focusing means. No continuous movement of the detection plane around the central best focus position (wobbling) is required.

According to a preferred embodiment exactly two images are acquired being located on different sides of the detection plane, preferably at equal distances. The control of the focusing means is therein adapted such that the amount of defocus for each imaging plane is substantially equal, eventually with a certain offset. Thus, by the merit function it is checked how much focused the image for each imaging plane is, and the focusing means is adapted such that the amount of defocusing for each imaging plane becomes substantially equal. If the patient moves during the analysis, this movement is continuously detected so that the focusing means are continuously readjusted automatically.

According to another preferred embodiment the imaging system comprises two cameras, for instance CCD-cameras or CMOS cameras, each being focused on one of the imaging planes. Both cameras simultaneously take an image of the object of interest. Thus only one microscope objective is required for focusing both the two cameras as well as the excitation beam onto the respective imaging plane or detection plane, respectively. Alternatively, only one camera can be used, in which embodiment the focus control means are adapted for time-resolved focusing of the camera on the at least two imaging planes, i.e. the at least two images of the object of interest are subsequently acquired, and focusing of the camera is continuously (alternately) changed between the at least two imaging planes. In the one-camera embodiment focus control means for time-resolved focusing of the camera on the at least two imaging planes, in particular for alternately focusing of the camera on the at least two imaging planes, are provided. These focus control means are thus only located in the light path of the imaging system and not in light path of the Raman system.

The used camera(s) can be standard color CCD camera if the different wavelength regions overlap with the different color regions (R,G or B) of the camera. It is also possible to use a CCD camera with specially designed color sensitivity for different pixels, or to use a dichroic mirror and two monochrome cameras. Instead of CCD cameras also other imaging devices can be used including: CMOS sensors (and photodiode arrays or scanning devices for other applications). For monochromatic OPSI a monochrome camera can be used.

The (relative) amount of defocus of the imaging system is preferably determined by use of a merit function. Examples for such merit functions are the standard deviation of pixel intensity in the whole image or a region of interest. When the system is focused sharp intensity transitions are washed out and the standard deviation decreases. Other examples are the sum or average of gradient of pixel intensities in the whole image or a region of interest. When the system is focused sharp intensity transitions are washed out and the gradient decreases. The (well known) Sobel gradient operator can calculate the gradient for example, however, other gradient operators are also possible.

Common auto-focusing methods also use merit functions. However, the way in which images at different depths are acquired according to the present invention is advantageous. As explained above, it is not possible to quantify the amount of defocus in an absolute sense if the object is not exactly known. In known auto-focusing methods the amount of focus is calculated for many settings of the system, and the best focus position corresponds to the position with the maximum merit value. It is proposed to measure the amount of focus at two image planes at least. The absolute values are not determined and evaluated, but only a relative value, e.g., the difference between the amount for the imaging planes.

Different embodiments for the monitoring beam source are possible. It is well possible to use only one single laser for emitting the monitoring beam, or a single white light source. Further, appropriate filters can be used to split up the generated white light beam into two or more monitoring beams having different colors. According to a preferred embodiment two separate light sources, in particular light emitting diodes (LEDs) are used emitting partial monitoring beams in different wavelength areas, which beams are combined by a beam combination unit into the monitoring beam for imaging the target region It is preferred that the monitoring system is adapted for orthogonal polarized spectral imaging as mentioned above and as described in WO02/057759 A1.

The invention can not only be used in an analysis apparatus as described above, but relates also to an optical tracking system for continuously tracking a point of a moving object, comprising a target system to be focused on the tracked point, a monitoring system, focusing means, defocus detection means and auto-focusing means as claimed in claim 12. The invention can be used in every system where an imaging system is used to locate and track a point, for example the focus of a laser beam or the detection volume of a spectroscopic system, continuously in 3 dimensions at a specific position in a moving target. Examples include: (biomedical) laser surgery, laser cutting, laser welding, laser shaving, photodynamic therapy, remote sensing, and target and tracking in military applications. Also the above described analysis apparatus could be regarded as including such an optical tracking system.

Figure 2:
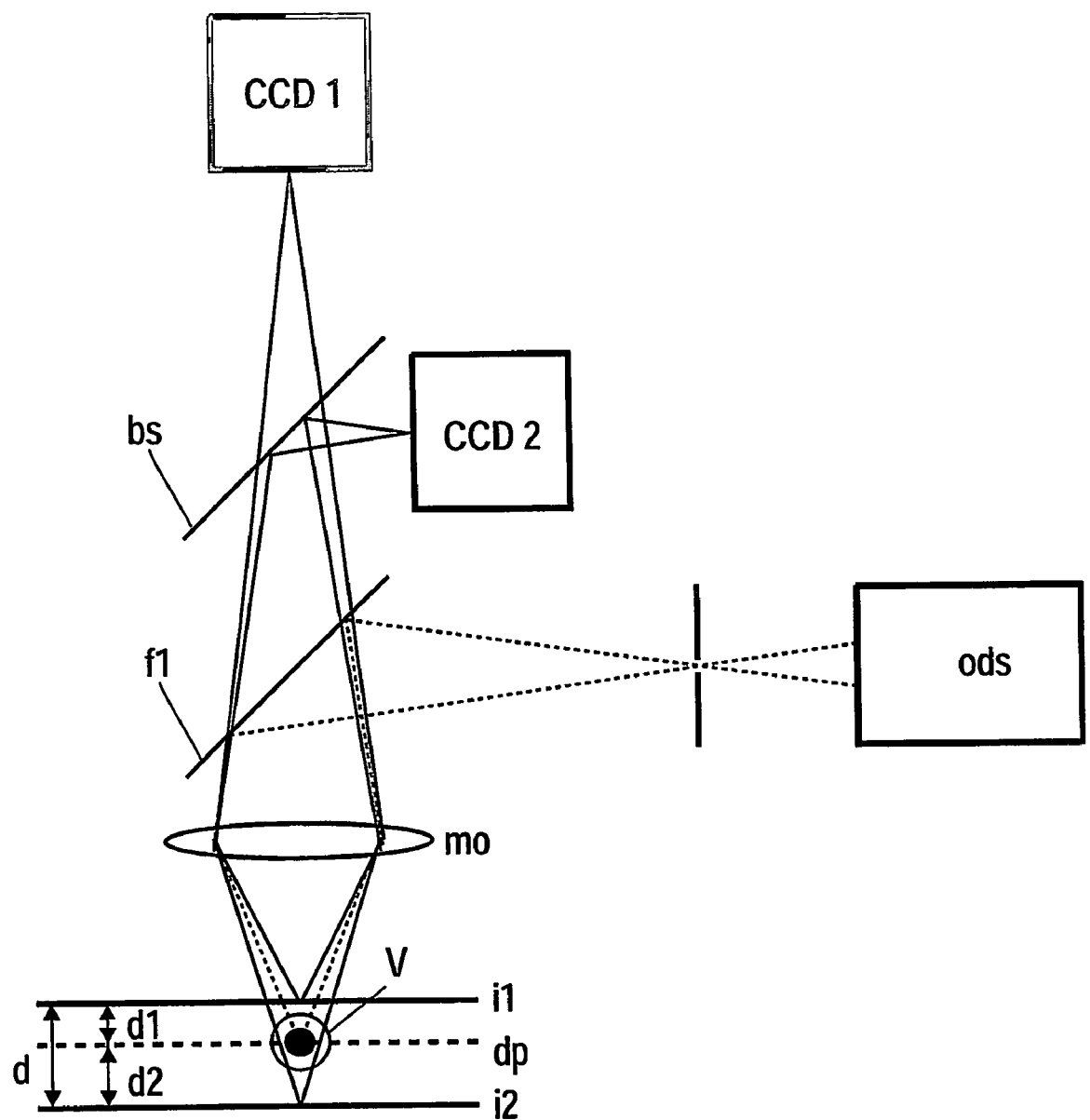
Figure 3:
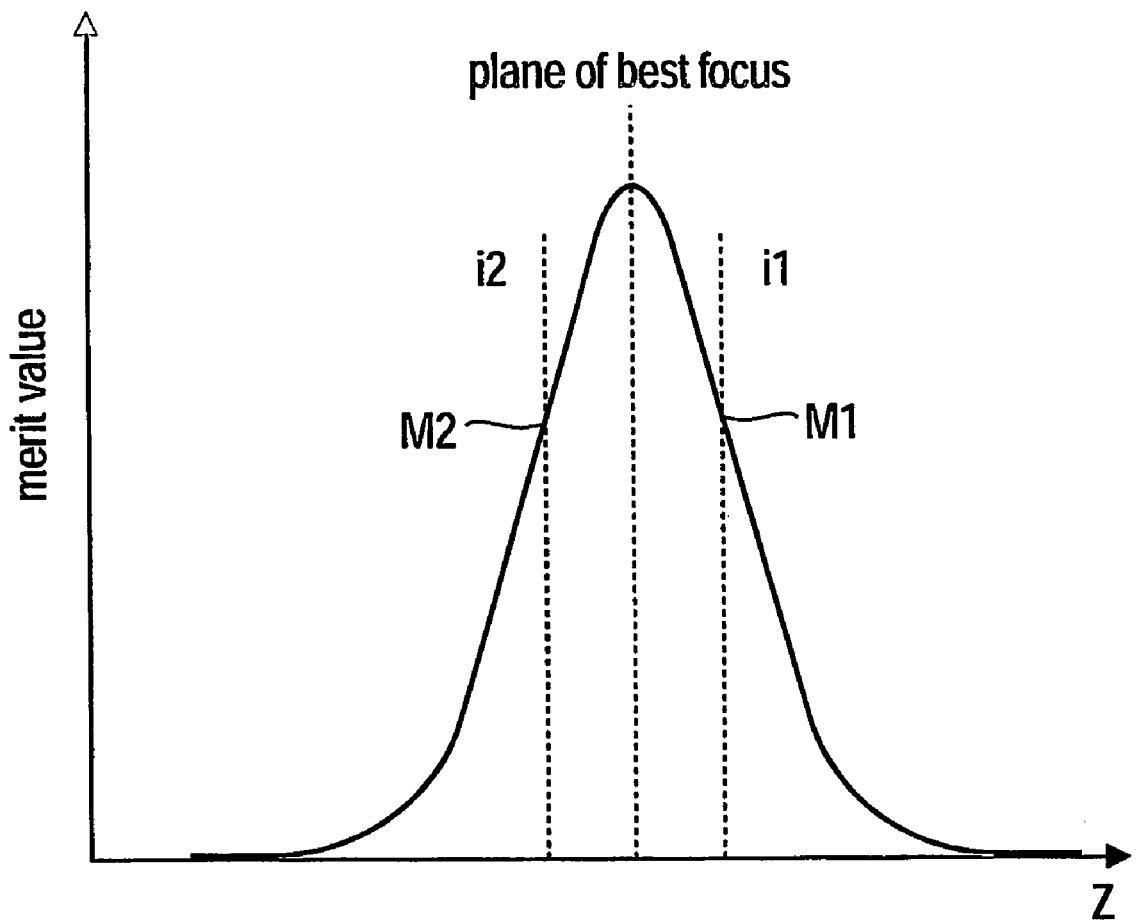
Figure 4:
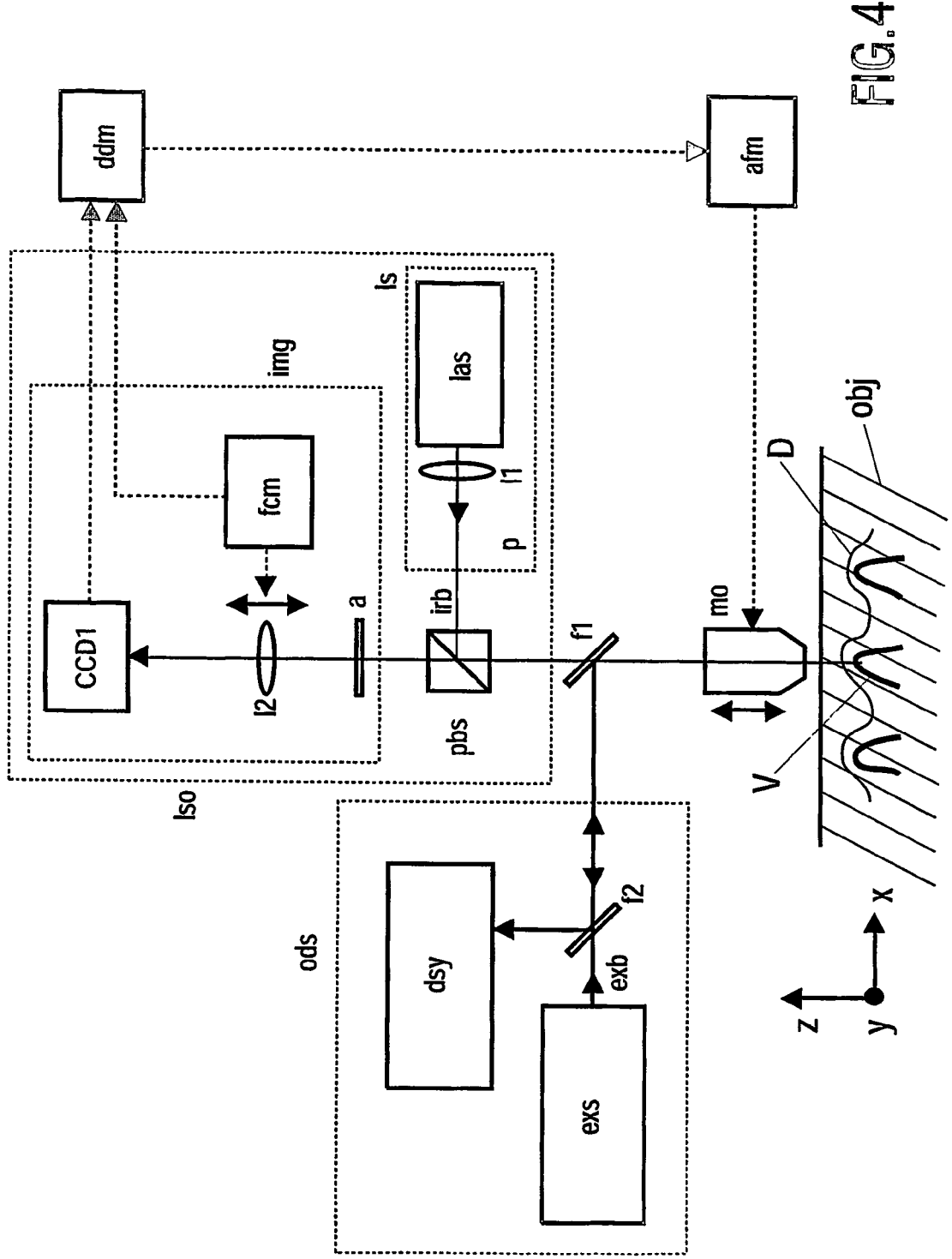

The invention will now be explained in more detail with reference to the drawings in which FIG. 1 shows a graphic representation of a first embodiment of an analysis system according to the present invention, FIG. 2 illustrates the principle used according to the present invention, FIG. 3 illustrates the use of a merit function, and FIG. 4 shows a graphic representation of a second embodiment of an analysis system according to the present invention.

FIG. 1 is a graphic representation of a first embodiment of an analysis system in accordance with the invention. The analysis system includes an optical monitoring system (lso) for forming an optical image of the object (obj) to be examined. In the present example the object (obj) is a piece of skin of the forearm of the patient to be examined. The analysis system also includes a multi-photon, non-linear or elastic or inelastic scattering optical detection system (ods) for spectroscopic analysis of light generated in the object (obj) by a multi-photon or non-linear optical process. The example shown in FIG. 1 utilizes in particular an inelastic Raman scattering detection system (dsy) in the form of a Raman spectroscopy device. The term optical encompasses not only visible light, but also ultraviolet radiation and infrared, especially near-infrared radiation.

The monitoring system (lso) comprises a monitoring beam source (ls) for emitting a monitoring beam (irb) and an imaging system (img) for imaging the target region, e.g. a blood vessel (V) in the upper dermis (D) of the patients forearm (obj). The monitoring beam source (ls) in this example comprises a white light source (las), a lense (l1) and an interference filter (not shown) to produce light in the wavelength region of 560-570 nm. Further, a polarizer (p) for polarizing the monitoring beam (irb) is provided. The monitoring beam source (ls) is thus adapted for orthogonal polarized spectral imaging (OPSI).

In OPSI polarized light is projected by a microscope objective (mo) through a polarizing beam splitter (pbs) onto the skin (obj). Part of the light reflects directly from the surface (specular reflection). Another part penetrates into the skin where it scatters one or more times before it is absorbed or is re-emitted from the skin surface (diffuse reflection). In any of these scattering events the polarization of the incident light is slightly changed. Light that is directly reflected or penetrates only slightly into the skin will scatter only one or a few times before it is re-emitted, and will mostly retain its initial polarization. On the other hand, light that penetrates more deeply into the skin undergoes multiple scattering events and is completely depolarized before re-emitted back towards the surface.

When looking at the object (obj) through a second polarizer or analyzer (A), oriented precisely orthogonal to that of the first polarizer (p), light reflected from the surface or the upper parts of the skin is largely suppressed, whereas light that has penetrated deep into the skin is mostly detected. As a result the image looks as if it were back-illuminated. Because wavelengths below 590 nm are strongly absorbed by blood, the blood vessels appear dark in the OPSI image.

Generally, an image is obtained using a monochrome CCD camera. Blood vessels are separated from other absorbing structures be means of size, shape, and movement of blood cells. The imaging system (img) used in the present embodiment comprises an analyzer (a) mentioned above for allowing only light having a polarization orthogonal to the light of the polarized monitoring beam (irb) to pass which is reflected back through the polarizing beam splitter (pbs) from the object (obj). Said light is further focused by a lens (12) and split up by a beam splitter (bs) for best reception by two CCD-cameras (CCD1, CCD2). These two cameras are focused on two different imaging planes within the object (obj) which will be used for auto-focusing as will be explained below in detail.

The Raman spectroscopy device (ods) comprises an excitation system (exs) for emitting an excitation beam (exb) and a detection system (dsy) for detection of Raman scattered signals from the target region. The excitation system (exs) can be constructed as a diode laser which produces the excitation beam in the form of an 785 nm infrared beam (exb). Of course other lasers can be used as excitation system as well. A system of mirrors and, for instance, a fiber conduct the excitation beam (exb) to a dichroic mirror (f1) for conducting the excitation beam (exb) along the monitoring beam (irb) to the microscope objective (mo) for focusing both beams onto the object (obj).

The dichroic mirror (f1) also separates the return (monitoring) beam from scattered Raman signals. While the reflected monitoring beam is transmitted to the imaging system (img), elastically and inelastically scattered Raman light from the object is reflected at the dichroic mirror (f1) and conducted back along the light path of the excitation beam. Inelastically scattered Raman light is then reflected by an appropriate filter (f2) and directed along the Raman detection path in the detection system (dsy) to the input of a spectrometer with a CCD detector. The spectrometer with the CCD detector is incorporated into the detector system (dsy) which records the Raman spectrum for wavelengths that are smaller than approximately 1050 nm. The output signal of the spectrometer with the CCD detector represents the Raman spectrum of the Raman scattered infrared light. In practice this Raman spectrum occurs in the wavelength range beyond 800 nm, depending on the excitation wavelength. The signal output of the CCD detector is connected to a spectrum display unit, for example a workstation that displays the recorded Raman spectrum (spct) on a monitor. Also a calculation unit (e.g. a workstation) is provided to analyze the Raman spectrum and calculate the concentration of one or more analytes.

Regarding further details of the analysis apparatus in general and the function thereof reference is made to the above mentioned WO 02/057759 A1.

The two cameras (CCD1, CCD2) are provided in the imaging system (img) to achieve continuous auto-focusing of the confocal Raman system (ods) in a blood vessel (V). This is required since patients will move during a blood analysis in lateral (z) as well as in transversal (x, y) directions. Therefore, continuous measurement and adjustment of the optimal location of the confocal detection center is required. Transversal movements can be easily detected by the imaging system, whereas axial movements are much more difficult to detect. According to the present invention the two cameras (CCD1, CCD2) thus take an OPS image of the blood vessel (V); however, the imaging planes of the two cameras are slightly separated in axial direction (z). This is shown in more detail in FIG. 2. While the first camera (CCD1) is focused onto a first imaging plane (i1) above and in parallel to the detection plane (dp) onto which the Raman excitation and detection system (exs, dsy) are focused, the second camera (CCD2) is focused onto a second imaging plane (i2) below and parallel to the detection plane (dp). The distance (d) between the two imaging planes (i1, i2) is in the order of or slightly larger compared to the depth of field of the objective (mo), in particular in the range from 0.5 to 20 μm. Preferably, the distances (d1, d2) of the imaging planes (i1, i2) from the detection plane (dp) are equal and fixed.

From the two images acquired by the two cameras (CCD1, CCD2) focused onto the separate imaging planes (i1, i2) the amount of defocus is measured by a defocus detection means (ddm) with a merit function for both cameras. Based on the determined difference in the amount of defocus and the known distances (d1, d2) between the imaging planes (i1, i2) and the detection plane (dp) the position of the microscope objective (mo) is adjusted by auto-focusing means (afm) such that the blood vessel (V) is imaged by both cameras (CCD1, CCD2) with an equal amount of defocus or, if that is beneficial, with a certain offset. With this information the Raman confocal detection volume can be continuously located exactly inside the blood vessel (V).

A merit function is thus used to calculate a single number from an image. Depending on the type of merit function, this number is maximal or minimal for certain images. A merit function for automatic focusing is preferably chosen in such a way that it has its extreme value at the sharpest images. The extreme value of the merit function, however, is different for different objects. Therefore, if the object is not exactly known, one cannot know if the image is properly focused from a single measurement. Only by comparing the outcome of the merit function for different settings of the system, one can determine the settings that result in the optimum focus. Shortly, one could say that if the object is not exactly known a merit function only has relative and no absolute meaning. Examples of a merit function are: Standard deviation of pixel intensity in the whole image or a region of interest. Sum of gradient of pixel intensities in the whole image or a region of interest. The Sobel gradient operator can calculate the gradient for example. Other gradient operators are also possible.

According to the present embodiment it is assumed that in the vicinity of the best focus position, the value of the merit function changes symmetrically above and below the best focus position. Therefore, if the merit function is calculated at two positions, and the outcome is equal, the optimum focus position must be located exactly in between these positions. If merit value 1 (M1; see FIG. 3) is larger compared to merit value 2 (M2) image plane 1 (i1) must be closer to the blood vessel compared to image plane 2 (i2) and the central focus plane has to shift upwards. Therefore, it is always known in which direction the focus position has to be shifted from the relatives values of M1 and M2. This is important for a robust implementation of the system. The typical shape of a merit function is illustrated in FIG. 3. In the current embodiment it is just detected if M1 is larger or smaller compared to M2. Depending on the outcome the detection plane (dp) is moved up or down by a fixed amount (e.g. 1 µm). This is the simplest embodiment. In a more advanced embodiment it is also possible to determine the size of the step from the difference of defocus.

The complete image can be used for auto-focusing. However, different blood vessels or parts thereof lie at different depths below the skin surface. Therefore, it is more accurate to use a region of interest around the best Raman measurement position for auto-focusing. In a different application with higher quality images, an accuracy of 1% of the depth of focus can be achieved with the method according to the present invention. Thus, for automatic focusing of the Raman excitation beam, the acquired accuracy in the order of 1 µm can be obtained.

Another embodiment of an analysis apparatus according to the present invention is shown in FIG. 4. While the optical detection system (ods) is identical the imaging system (img). In the imaging system (img) only one CCD-camera (CCD1) is provided which, however, is adapted for time-resolved reception of images from the target region at different imaging planes. This can be achieved by continuously changing the focus of the camera (CCD1) between the first and the second imaging plane (i1, i2) by variation of the position of the lens (l2) controlled by focus control means (fcm). Thus, also with one camera the amount of defocus for different imaging planes can be determined by use of a merit function as explained above so that finally also with this embodiment auto-focusing of the confocal Raman system in the blood vessel (V) can be achieved.

Alternatives for continuously changing the focus of the camera (CCD1) are to move the camera or to use a switchable lens based on electro wetting.

In the above monochromatic OPSI embodiments are described having a white light source and a filter. Nevertheless, the invention can be applied in many different embodiments including:

a) Monochrome OPSI embodiments having a single light source with wavelength below 590 nm, where the light source can be narrowband (LED, laser(diode)) or broadband (lamp), with a filter and having a monochrome image module (CCD camera, CMOS sensor);

b) Bichromatic/multichromatic OPSI embodiments (in principle more than two colors can be used to extract extra information from the images) having b1) a single light source with two colors, one above 600 and one below 590 nm, which can be done by placing a filter with two transmission regions in front of a white light source or by using a special light source that emits two different colors (e.g. a LED with two colors); it is also possible to use two or more light sources with different colors and a beam combiner;

b2) a color camera or sensor, with different pixels sensitive to the colors of the different light sources; this can be the normal RGB sensitivity curves or special curves (by special filters per set of pixels); it is also possible to use a dichroic mirror and two monochrome image sensors;

b3) a single broadband (white) light source and use one color camera with special sensitivity curves corresponding to different wavelength regions for the different pixels; alternatively, a dichroic mirror and two monochrome cameras with special filters in the optical path can be used;

b4) a single light source with a switchable spectrum or two light sources that emit light in different wavelength regions that are switched on alternately; a monochrome camera can then be used to capture the images with different colors alternatively.

Compared to known auto-focusing techniques, the method according to the present invention has the advantage that the confocal detection volume can be continuously located in the center of the blood vessel in which the blood shall be analyzed. The images that are compared are preferably measured simultaneously. Further, no moving elements are required in the two-camera embodiment, and a single high numerical aperture objective can be used for the monitoring system and the optical detection system.

The invention claimed is:

1. An analysis apparatus, in particular a spectroscopic analysis apparatus, for analyzing an object comprising:
   an excitation system comprising a first source for emitting an excitation beam to excite a target region;
   a monitoring system comprising a second different source for emitting a monitoring beam and an imaging system to image the target region;
   a detection system for detecting scattered radiation from the target region generated by the excitation beam;
   focusing means for focusing the imaging system on at least two substantially parallel imaging planes within the object at a predetermined distance and for focusing the excitation system and the detection system on a detection plane within the object substantially parallel and in-between the imaging planes at predetermined distances;

defocus detection means for determining an amount of defocus of the imaging system flour the detection plane for the at least two imaging planes; and auto-focusing means for controlling the focusing means to commonly change the focusing of the imaging system, the excitation system and the detection system based on the determined amount of defocus and the predetermined distances between the imaging planes and the detection plane such that a difference between the determined amount of defocus for the at least two imaging planes equals a predetermined amount.

2. An analysis apparatus as claimed in claim 1, wherein the focusing means are adapted for focusing the imaging system on two imaging planes at equal distances to the detection plane and wherein the auto-focusing means are adapted for controlling the focusing means such that the amount of defocus for each imaging plane is substantially equal.

3. An analysis apparatus as claimed in claim 1, wherein the imaging system comprises two cameras each being focused on one of the imaging planes.

4. An analysis apparatus as claimed in claim 1, wherein the imaging system comprises one camera and focus control means for time-resolved focusing of the camera on the at least two imaging planes, in particular for alternately focusing of the camera on the at least two imaging planes.

5. An analysis apparatus as claimed in claim 1, wherein the defocus detection means are adapted to determine the amount of defocus by use of a merit function.

6. An analysis apparatus as claimed in claim 5, wherein said merit function is the sum or average over all pixels in the image or a region of interest of the intensity gradient, in particular as determined by the Sobel gradient operator.

7. An analysis apparatus as claimed in claim 1, wherein the second source comprises two light sources fox emitting partial monitoring beams in different wavelength areas and a beam combination unit for combining the partial monitoring beams into the monitoring beam.

8. An analysis apparatus as claimed in claim 1, wherein the second source comprises a single white light source having a filter for transmitting light in two separate wavelength regions and wherein the imaging system comprises imaging means for color sensitive detection.

9. An analysis apparatus as claimed in claim 1, wherein the second source comprises a single light source with wavelength below 590 nm, said light source being a narrowband or broadband light source, a filter and a monochrome imaging system.

10. An analysis apparatus as claimed in claim 1, wherein the monitoring system is adapted for orthogonal polarized spectral imaging.

11. An analysis method, in particular a spectroscopic analysis method, for analyzing an object comprising the steps of:

emitting an excitation beam from a first source to excite a target region;

emitting a monitoring beam from a second different source to image the target region by an imaging system;

detecting scattered radiation from the target region generated by the excitation beam, focusing the imaging system on at least two substantially parallel imaging planes within the object at a predetermined distance;

focusing the excitation system and the detection system on a detection plane within the object substantially parallel and in-between the imaging planes at predetermined distances;

determining an amount of defocus of the imaging system from the detection plane for the at least two imaging planes; and controlling the focusing to commonly change the focusing of the imaging system, the excitation system and the detection system based on the determined amount of defocus and the predetermined distances between the imaging planes and the detection plane such that a difference between the determined amount of defocus for the at least two imaging planes equals a predetermined amount.

12. An optical tracking system for continuously tracking a point of a moving object, comprising:

a target system comprising a first source emitting a light beam to be focused on the tracked point;

a monitoring system comprising a second different source for emitting a monitoring beam and an imaging system to image the target region;

focusing means for focusing the imaging system on at least two substantially parallel imaging planes within the object at a predetermined distance and for focusing the target system on a detection plane within the object substantially parallel and in-between the imaging planes at predetermined distances;

defocus detection means for determining an amount of defocus of the imaging system from the detection plane for the at least two imaging planes; and auto-focusing means fox controlling the focusing means to commonly change the focusing of the imaging system and the target system based on the determined amount of defocus and the predetermined distances between the imaging planes and the detection plane such that a difference between the determined amount of defocus for the at least two imaging planes equals a predetermined amount.

13. An optical tracking system as claimed in claim 12, wherein said first source comprises a light beam generation means for emitting said light beam, in particular a laser for emitting a laser beam, to be focused on the tracked point of the object.

14. The optical tracking system as claimed in claim 12, wherein the focusing means are adapted for focusing the imaging system on two imaging planes at equal distances to the detection plane and wherein the auto-focusing means are adapted for controlling the focusing means such that the amount of defocus for each imaging plane is substantially equal.

15. The optical tracking system as claimed in claim 12, wherein the imaging system comprises two cameras each being focused on one of the imaging planes.

16. The optical tracking system as claimed in claim 12, wherein the imaging system comprises one camera and focus control means for time-resolved focusing of the camera on the at least two imaging planes, in particular for alternately focusing of the camera on the at least two imaging planes.

17. The optical tracking system as claimed in claim 12, wherein the defocus detection means are adapted to determine the amount of defocus by use of a merit function.

18. The optical tracking system as claimed in claim 17 wherein said merit fraction is the sum or average over all pixels in the image or a region of interest of the intensity gradient, in particular as determined by the Sobel gradient operator.

19. The optical tracking system as claimed in claim 12, wherein the second source comprises two light sources for emitting partial monitoring beams in different wavelength areas and a beam combination unit for combining the partial monitoring beams into the monitoring beam.

20. The optical tracking system as claimed in claim 12, wherein the second source comprises a single white light source having a filter fox transmitting light in two separate wavelength regions and wherein the imaging system comprises imaging means for color sensitive detection.

* * * * *